United States Patent [19]

Dussourdd'Hinterland et al.

[11] 4,083,961
[45] Apr. 11, 1978

[54] PLASMINOGEN ACTIVATOR PHARMACEUTICAL COMPOSITIONS

[75] Inventors: Lucien Dussourdd'Hinterland, Castres; Lucien Pradayrol, Toulouse; Jacques Durand; Gerard Normier, both of Castres, all of France

[73] Assignee: Pierre Fabre S.A., Paris, France

[21] Appl. No.: 682,283

[22] Filed: May 3, 1976

[30] Foreign Application Priority Data

May 5, 1975    France .................................. 75 13932

[51] Int. Cl.² .................... A61K 35/12; A61K 31/715
[52] U.S. Cl. ...................................... 424/95; 424/94; 424/103; 424/104; 424/105; 424/180
[58] Field of Search ................. 424/180, 95, 103, 104, 424/105, 94

[56]  References Cited
PUBLICATIONS

Szentklaray et al.—Chem. Abst., vol. 73 (1970) p. 118,099z.
Gelin—Chem. Abst., vol. 72 (1970) p. 30189x.

*Primary Examiner*—Sam Rosen
*Attorney, Agent, or Firm*—Alan H. Levine

[57]     ABSTRACT

The present invention relates to a pharmaceutical composition comprising a plasminogen activator and a polysaccharide sulphate. The invention also covers a process for preparing the pharmaceutical composition and a process for preparing the plasminogen activator.

The pharmaceutical compositions are useful in the treatment of circulatory disorders such as venous thromboses.

11 Claims, No Drawings

PLASMINOGEN ACTIVATOR PHARMACEUTICAL COMPOSITIONS

BACKGROUND OF THE INVENTION

1. Field of the Invention

The present invention relates to a pharmaceutical compositions, more particularly to pharmaceutical compositions consisting essentially of a plasminogen activator and a polysaccharide sulphate. The present invention also relates to a process for preparing the pharmaceutical composition and to a process for preparing the plasminogen activator.

2. Description of the Prior Art

An activator of the type with which the present invention is concerned is urokinase, which is extracted from the urine of mammals (cp. U.S. Pat. Nos. 2,961,382; 2,983,647 and 2,989,440). However, it has been found that urokinase is very sensitive to induced inhibitors and that its effect diminished very quickly on inhibition. The Applicants in U.S. Ser. No. 529,147 now U.S. Pat. No. 3,998,947 described a process for extracting a novel plasminogen activator from animal organs which was at least equivalent to urokinase in regard to activity but which was unaffected by inhibitors.

SUMMARY OF THE INVENTION

The Applicants have now found that the activity of plasminogen activators, and particularly the plasminogen activator prepared by the process claimed is U.S. Ser. No. 529,147, may be powerfully potentiated by combining it with a polysaccharide sulphate.

DESCRIPTION

This invention relates to a pharmaceutical composition consisting essentially of a plasminogen activator and a polysaccharide sulphate.

In one embodiment the plasminogen activator is obtained by a process comprising the following steps:
(a) suspending a powdered acetone extract of animal organs in an aqueous saline solution having a low ionic strength and a pH around the neutral point;
(b) taking up the precipitate obtained in step (a) in an aqueous saline solution having an ionic strength of from about 0.6 to about 1 at pH-values of from about 3 to about 5;
(c) precipitating out from the solution obtained in step (b), after decantation thereof, by adding a salt or an organic solvent at a pH of from about 3 to about 5;
(d) taking up the precipitate obtained in step (c) in water or a saline solution, followed by reprecipitation by adding a salt at a pH of, or slightly above 7;
(e) taking up the precipitate obtained in step (d) in water and dialysing the solution up to a resistivity level about 1000 ohm. cm at 10° C, and
(f) optionally purifying the solution obtained.

The polysaccharide sulphate used may be a sulphate of dextran preferably having a molecular weight of between about 3000 and about 15,000 and containing between about 10% and about 20% of sulphur.

This polysaccharide may be used either as a simple association with the plasminogen activator, obtained by simply mixing the two products, or as a complex compound two products, or as a complex compound with the activator. Tests have shown that the activity of the simple association is similar to that of the complex.

The polysaccharide sulphate is preferably used in a quantity of between about 10 and about 30% by weight of activator calculated as protein and more preferably about 20% by weight of activator, calculated as protein.

The polysaccharide sulphate used may be prepared by any known process, for example by esterification of the polysaccharide by a mineral or organic acid of sulphur in the presence of a base for fixing the water. Thus, the dextran sulphate may be prepared by degradation of dextran in heat in a sulphuric acid medium to reduce the molecular weight of dextran, followed by esterification of the resulting dextran with chlorosulphonic acid in pyridine.

If the pharmaceutical composition is to be prepared in the form of a complex, formation of the complex is carried out at a pH close to neutrality by adding the necessary quantity of polysaccharide sulphate to the activator in solution, and the pH of the solution is then progressively lowered to about 6 to precipitate the desired complex. When the precipitate has been recovered, it may be redissolved in a buffer solution at a pH close to 7 and freeze dried.

In the process of complex formation, phosphoric acid is preferably used to lower the pH of the solution and precipitation is carried out at a temperature in the region of 40° C.

The present invention relates also to an improved process for the preparation of the plasminogen activator.

This process, like that described in U.S. Ser. No. 529,147 consists of treating a powered acetone extract of animal organs selected from the group consisting of pig lungs, calf lungs, ox lungs, horse lungs, lamb lungs, sheep lungs, pig kidneys, calf kidneys, ox kidneys, horse kidneys, lamb kidneys, sheep kidneys, pig ovaries, cow ovaries and sheep ovaries comprising the steps of:
(a) suspending the powered acetone extract in an acetate buffer which has a dissociation constant of between about 0.01 and about 0.1 and a pH close to neutrality;
(b) taking up the precipitate obtained in stage a) in an acetate buffer having a dissociation constant between about 0.6 and about 1 and a pH of between about 3 and about 5;
(c) precipitating the solution obtained after decanting the product from stage b) by adding a salt at a pH of between about 3 and about 5;
(d) taking up the precipitate obtained in stage c) in an acetate buffer and precipitating by the addition of a salt at a pH of between about 7 and about 8;
(e) precipitating the solution obtained after clarifying the product from stage d) by addition of a salt at a pH close to neutrality;
(f) pyrifying the resulting precipitate.

The purification stage (f) is preferably carried out by precipitating the activator at the isoelectric point, that is to say at a pH of between about 6.3 and about 6.5 and a resistivity of the solution of about 450 ohm.cm, and chromatographing the resulting precipitate after it has been redissolved. The chromatographic process employed is preferably an affinity chromatography.

As in the presence described in USSN 529,147 the salt used for carrying out the precipitation in stages (c), (d) and (e) is preferably crystalline ammonium sulphate. In stage (c), ammonium sulphate is used at a concentration of between about 200 and about 300 g/l and in stages (d) and (e) at a concentration of between about 60 and about 80 g/l.

The plasminogen activator preferably used is one which acts on the peptide arginine-valine bonds in the plasminogen by opening these bonds without breaking the disulphide bridges. The plasminogen activator preferably has a molecular weight of about 40,000 and an isoelectric point of about 6.8.

A general method of preparing a complex plasminogen activator according to the present invention is outlined below to illustrate the preferred method of carrying out the invention and to bring out more clearly certain characteristics of the present invention, without, however, restricting it.

The powered acetone extract which constitutes the basic starting material for preparing the plasminogen activator is preferably prepared as follows:

The defrosted and crushed organs are dispersed in an acetone bath at a temperature below about −10° C and vigorously stirred. The resulting suspension is filtered and the filter cake obtained is rinsed with acetone before being dried under nitrogen.

(a) Preliminary Washing

The powered acetone extract is suspended in an acetate buffer which has a dissociation constant of the order of 0.02, the pH of the solution being close to neutrality. The solution is stirred for about one hour at about 4° C and the residue of powder is then freed from surplus liquid and the supernatant solution is removed.

(b) Extraction

The residue is suspended in an acetate buffer having a pH of between about 3 and about 5 and the suspension is stirred for about 3 hours at about 4° C. After removal of liquid, the residue of unextracted powder is discarded and the solution which is recovered is taken to be clarified.

(c) First Precipitation in an Acid Medium

The clarified extract obtained in stage (b) is precipitated in an acid medium at a pH of about 4.5 by the addition of ammonium sulphate at a concentration of between about 290 and about 300 g/l. The precipitate obtained in this way is taken up in a solution of acetate buffer and the pH of this solution is then adjusted to between about 7 and about 8 with concentrated sodium hydroxide.

(d) Second Precipitation in a Slightly Alkaline Medium

The solution described above is reprecipitated by the addition of ammonium sulphate at a concentration of between about 60 and about 80 g/l. After treatment in the clarifier, the inactive precipitate is discarded and the solution is adjusted to a pH of about 7.

(e) Third Precipitation in the Region of Neutrality

The solution obtained as described above is precipitated a third time by the addition of ammonium sulphate at a concentration of between about 60 and about 80 g/l. The resulting precipitate is taken to the clarifier and washed with distilled water until neutral.

The precipitate obtained in this way is dispersed in distilled water and the solution is acidified to about pH 4. After centifuging, the supernatant layer is recovered and diluted several times with distilled water until it has a resistivity of about 600 to about 650 Ohm.cm.

The pH of the solution is then adjusted to between about 6.3 and about 6.5, the resistivity being then of the order of 450 Ohm.cm.

The precipitate obtained is recovered by centrifuging and then dispersing in a phosphate buffer. The pH of the solution, which is at that stage close to neutral, is raised to between about 9 and about 10 by addition of the base and then returned to neutrality.

The centrifuged solution is then recovered and used for carrying out affinity chromatography.

The chromatography support used is of the type AH-Sepharose 4B on which has previously been coupled a specific inhibitor of plasminogen activator by a carbodiimide.

Inhibitors which may be used for this purpose include ε-aminocaproic acid, aminoethyl cyclohexanoic acid, trans-4-aminoethylcyclohexane carboxylic acid and para-aminomethylbenzoic acid.

Affinity chromatography may equally well be carried out on a sepharose support activated to CNBr on which lysine or one of the products mentioned above may be fixed.

It should be understood that in fact any other supports on which coupling can be carried out may be used, for example supports of the Biogel series.

Elution is now carried out on the fraction left on the support by means of a gradient of dissociation constant, and the protein content and activity of the eluate are determined by the methods described hereinafter.

A polysaccharide sulphate is added to the resulting solution at approximately neutral pH in a quantity equal to about 20% of the quantity of proteins present in the solution. The solution is progressively acidified to pH values close to 6. The activator then precipitates in the form of a complex with the polysaccharide sulphate. The precipitate is recovered by centrifuging and then dissolved in a buffer at a pH of about 7 after it has been freeze dried.

The following example is presented for illustrative purposes only and should not be construed as limiting the present invention which is properly delineated in the claims.

EXAMPLE 10 kg of sows' ovaries kept at −20° C were defrosted to −5° C and then crushed with a meat grinder having a grid of 5 mm. The crushed tissue was then dispersed in 75 l of acetone at −20° C. After vigorous stirring for 1 hour, the suspension was filtered on a Bunchner funnel and the filter cake on the funnel was rinsed with acetone at −20° C. The cake was then removed from the funnel and dried in a column under an ascending stream of dry nitrogen. 1.3 kg of acetonic powder which could be kept at 4° C was obtained.

(a) The acetonic powder obtained in this way was suspended in 30 l of M/100 acetate buffer, pH 6.5. The suspension was vigorously stirred for 1 hour at 4° C and then freed from liquid. The organs were recovered and the filtrate discarded. The organs were then again suspended in 10 l of the same acetate buffer and stirred for 15 minutes at 4° C before being dried.

(b) After this drying, the organs were suspended in 30 l of 0.3 M acetate buffer (pH 4.2) at 4° C and the whole suspension was gently stirred for 3 hours at 4° C. The liquid was then separated and the organs were discarded. The filtrate was then passed through the clarifier to remove fine particles in suspension and the clarified extract was collected.

(c) 250 g/l of crystalline ammonium sulphate were added to this extract which was then shaken until completely dissolved and left to stand overnight at 4° C.

The precipitate was removed to be clarified and the mother liquors were discarded. The precipitate was then redissolved by stirring it for one hour in 8 l of 0.1 M acetate buffer, pH 4.2, at 4° C. The pH of the solution was then raised to 7.5 by the addition of concentrated sodium hydroxide.

(d) When the solution was being adjusted to pH 7.5, 64 g per 1 of crystalline ammonium sulphate were added and the pH was then lowered to 7.2 with acetic acid. The solution was then left to stand at 4° C for 30 minutes. After treatment in the clarifier, the inactive precipitate was discarded and the clarified solution was adjusted to pH 6.5.

(e) 72.5 g per 1 of ammonium sulphate were then added to this solution while the pH was kept constant with normal sodium hydroxide. The mixture was stirred until completely dissolved and then left to stand at 4° C for one hour 30 minutes. After clarification, the solution was discarded and the precipitate was washed on the clarifier by passing 2.5 l of distilled water through it until neutral.

(f) The precipitate was then dispersed in 500 ml of distilled water.

Dilute acetic acid was added until a stable ph of 4.3 was obtained and the mixture was then stirred for one hour at 4° C. After centrifuging, the insoluble constituents were discarded and the supernatant liquid was diluted to 5 to 8 times its volume with distilled water until it had a resistivity of 600 to 650 Ohm.

The pH of the supernatant liquid taken up was then adjusted to pH 6.3 to 6.5 with 0.5 N soda, the resistivity thereby falling to 450 Ohm. The precipitate formed was immediately collected by centrifuging and the supernatant liquid was discarded.

This precipitate was dispersed in 200 ml of M/15 phosphate buffer, pH 7.2, at 4° C and the pH was then raised to 9.5–10 with sodium hydroxide (3 N). The dispersion was stirred vigorously for 20 minutes before being adjusted to pH 7.3 with dilute phosphoric acid. It was then left to stand for 30 minutes and centrifuged.

The insoluble component was then discarded and the superantant layer passed over a column containing a support of the type AH Sepharose 4 B.

After determination of the protein content (between 2.5 and 3 mg/ml), glycocol was added in an amount equal to twice the weight of the proteins, and the activity was then determined. From 0.5 to 0.6 g of proteins containing between 3000 and 4000 u.CTA/mg were obtained at this stage.

After determination of the proteins and the activity, dextran sulphate was added to the active fraction. The pH of the solution was then progressively lowered to pH 5.8–5.9 with dilute phosphoric acid. The product was left to stand for 30 minutes at 4° C and then centrifuged. The precipitate was recovered and the supernatant layer discarded. The complex was then dissolved in a buffer at pH 7–7.5 and freeze dried.

The method of operation and methods of determination employed for obtaining the experimental results are given below.

The fibrinolytic activity of an activator can be demonstrated in vivo on the rat by measuring the time of lysis of the plasma euglobulins. This technique is simple, reproducible and applicable to small laboratory animals and is suitable for the mechanism of activity of the product to be studied.

Principle

The determination of the time required for lysis of a clot of plasma euglobulins is a sensitive method giving a good indication of the overall lytic activity.

Lowering the ionisation constant of plasma by dilution with distilled water at acid pH, causes the euglobulins to be precipitated while the pseudoglobulins are left in the supernatant liquid.

The antiplasmins which inhibit fibrinolysis are also removed in this supernatant layer (hence the greater sensitivity of this method). The precipitated euglobulins contains practically the whole of the fibrinogen, plasminogen and plasminogen activator.

Technique

To obtain sample:

Blood collected on trisodium citrate 5.5 $H_2O$ at 3.8% in the ratio of 1/5 (as soon as the blood sample has been taken, it must be kept on melting ice and the test must be carried out within one hour of taking the blood sample). The plasma is obtained by centrifuging at high speed for 10 minutes.

Reagents

Michaelis buffer pH 7.35 (supplied from STAGO Laboratories),

Acetic acid, 1.6% solution diluted to 1/100 when required with distilled water cooled to 4° C, Thrombase solution containing 20 Mellanby units per ml in 0.05 M calcium chloride. 1 Ampoule of ROUSSEL thrombase containing 500 Mellanby units is taken up in 25 ml of 0.05 M $CaCl_2$, $CaCl_2$ 0.05 M (5 ml of $CaCl_2$ 0.25 M (STAGO) + 20 ml distilled water).

The thrombase solution prepared in this way is divided into two portions of 2 ml each which are kept in the freezer and defrosted when required.

Method

Introduce 0.5 ml of plasma into a conical centrifuge tube;

slowly add with stirring 9.5 ml of 0.016% acetic acid solution cooled to 4° C;

mix by shaking on parafilm;

leave to stand 20 minutes at 4° C;

centrifuge 10 minutes at 3500 revs/min;

discard supernatant layer;

empty tubes by turning them out over filter paper;

carefully dry the walls of the tube but avoid touching the precipitate stuck to the bottom of the tube;

take up the clot of euglobulins with 0.5 ml of Michaelis buffer;

when the clot has completely dissolved, transfer 0.25 ml of the solution of euglobulins to a hemolysis tube;

heat on a water bath to 37° C;

recalcify with 50 μm of calcium thrombase (at 20 U/ml);

start stopwatch as soon as coagulation begins;

observe the clot at regular intervals and note the time taken to complete decoagulation (appearance of snowflakes in clear liquid).

Animal Experiments

Male rats of the strain "Iffa-Credo" which have been fasting for about 16 hours and weigh between 180 and 250 gram, according to the experiments carried out, are divided into equal batches of control rats and treated rats.

The control rats are given, by injection into the dorsal vein of the penis, 1 ml per 100 gram of body weight of either pH 7.2 phosphate buffer or physiological serum, according to whether the product to be studied is dissolved in one or other of these vechicles.

The treated rats are given, by injection into the dorsal view of the penis, 1 ml per 100 gram of body weight, of the product to be studied, dissolved at the necessary concentration for obtaining the desired dose.

Precisely 15 minutes after the various injections, the rats are lightly anaesthetised with ether, the thorax is opened and the blood is removed by direct puncture into the ventricle. The blood is then treated by the technique described above.

The results obtained are shown below.

The dextran sulphate used in the test is potassium hydrodextran of the formula:

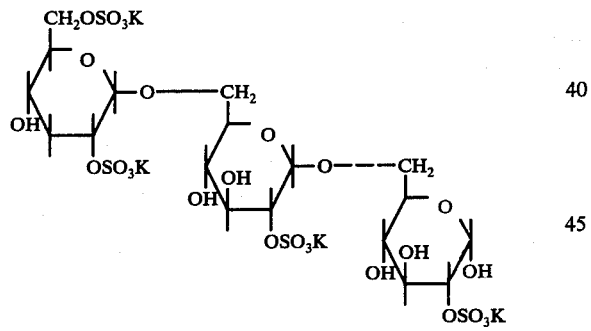

TEST 1

Activity of dextran sulphate

|  | Time for lysis in min |  |  |  |  |  | Average |
|---|---|---|---|---|---|---|---|
| Controls | 115 | 120 | 85 | 108 | 115 | 108 | 108.5 |
| Dextran sulphate 1 mg/kg | 73 | 120 | 110 | 110 | 50 | 120 | 98.1 |

-continued

|  | Time for lysis in min |  |  |  |  |  | Average |
|---|---|---|---|---|---|---|---|
| Dextran sulphate 2 mg/kg | 93 | 105 | 100 | 95 | 90 | 108 | 98.5 |

As can be seen from the figures, dextran sulphate given in the experimental doses has not significant activity.

TEST 2

Comparison of the activities of the activator used along and of the combination according to the invention.

For all the tests, the doses indicated for the activator are the doses in protein.

This test was carried out as a blind test.

|  | Time for lysis in min |  |  |  |  |  | Average | % action |
|---|---|---|---|---|---|---|---|---|
| Controls | 120 | 155 | 120 | 135 | 130 | — | 128 | — |
| Activator 10 mg/kg | 70 | 85 | 100 | 100 | 85 | 92 | 88.7 | 30.7 |
| Activator 10 mg/kg + dextran sulphate 2 mg/kg | 65 | 52 | 45 | 45 | 35 | — | 48.4 | 62.1 |

The solution according to the invention is significantly two times more active than the activator solution alone.

TEST 3

|  | Lysis time in min |  |  |  |  |  | Average | % action |
|---|---|---|---|---|---|---|---|---|
| Controls | 145 | 135 | 130 | 145 | 150 | 140 | 140.8 | — |
| Activator 5 mg/kg | 125 | 115 | 120 | 105 | 110 | — | 115 | 18.3 |
| Activator 5 mg/kg + dextran sulphate 1 mg/kg | 85 | 100 | 85 | 70 | 75 | 100 | 85.8 | 39 |

The results are the same as in Test 2.

TEST 4

|  | Lysis time in min |  |  |  |  |  | Average | % action |
|---|---|---|---|---|---|---|---|---|
| Controls | 83 | 80 | 75 | 65 | 95 | — | 79.6 | — |
| Activator 5 mg/kg | 67 | 100 | 100 | 65 | 70 | 85 | 81.2 | — |
| Activator 5 mg/kg + dextran sulphate 1 mg/kg | 48 | 53 | 48 | 55 | 55 | 50 | 51.5 | 35.3 |

At the dose employed, neither the active fraction nor the dextran sulphate used has any significant activity but the combination of the two shows a high activity, which is significant of the order of 35%.

TEST 5

Comparison between the activity of the simple association and of the complex according to the invention.

|  | Lysis time in min |  |  |  |  |  | Average | % action |
|---|---|---|---|---|---|---|---|---|
| Controls | 145 | 140 | 135 | 103 | — | — | 130.75 | — |
| Complex | 85 | 70 | 95 | 75 | 95 | 90 | 85 | 35 |
| Association | 85 | 80 | 85 | 95 | 80 | — | 85 | 35 |

It is found that the activities of the simple association and of the complex are practically the same.

It is quite clear from the above tests that the association of a polysaccharide sulphate and a plasminogen activator constitutes a medicament of choice for the treament of numerous circulator accidents such as in particular arterial or venous thromboses.

We claim:

1. A pharmaceutical composition consisting essentially of a plasminogen activator obtained by a process comprising the following steps:
   (a) suspending a powdered acetone extract of animal organs in an aqueous saline solution having a low ionic strength and a pH around the neutral point;
   (b) taking up the precipitate obtained in step (a) in an aqueous saline solution having an ionic strength of from about 0.6 to about 1 at pH-valves from about 3 to about 5;
   (c) precipitating out from the solution obtained in step (b), after decantation thereof, by adding a salt or an organic solvent at a pH of from about 3 to 5;
   (d) taking up the precipitate obtained in step (c) in water or a saline solution, followed by reprecipitation by adding a salt at a pH of, or slightly above 7;
   (e) taking up the precipitate obtained in step (d) in water and dialysing the solution up to a resistivity level of about 1000 ohm. cm at 10° C and
   (f) optionally purifying the solution obtained and adding a dextran sulfate in an amount effective to potentiate the plasminogen activator.

2. A pharmaceutical composition according to claim 1 in which the dextran sulphate has a molecular weight of between about 3000 and about 15000 and contains between about 10 and about 20% of sulphur.

3. A pharmaceutical composition according to claim 1 in which the dextran sulphate is used in an amount of between about 10 and about 30% by weight of the activator determined as protein.

4. A pharmaceutical composition according to claim 1 in which the plasminogen activator and the dextron sulphate are prepared in the form of a complex by addition of the dextron sulphate to the activator in a solution at a pH close to neutrality and the complex is then precipitated by acidification of the solution to a pH of about 6.

5. A pharmaceutical composition consisting essentially of a plasminogen activator obtained by:
   (a) suspending a powdered acetone extract of animal organs selected from the group consisting of pig lungs, calf lungs, ox lungs, horse lungs, lamb lungs, sheep lungs, pig kidneys, calf kidneys, ox kidneys, horse kidneys, lamb kidneys, sheep kidneys, pig ovaries, cow ovaries and sheep ovaries in an acetate buffer having a dissociation constant of between about 0.01 and about 0.1 and a pH close to neutral;
   (b) taking up the precipitate obtained in stage (a) in an acetate buffer having a dissociation constant of between about 0.6 and about 1 and a pH of between about 3 and about 5;
   (c) precipitating the solution obtained after decanting in stage (b) by addition of a salt at a pH of between about 5 and about 5;
   (d) taking up the precipitate obtained at stage (c) in an acetate buffer and precipitating by addition of a salt at a pH of between about 7 and about 8;
   (e) precipitating the solution obtained after clarification at stage (d) by additon of a salt close to neutrality;
   (f) purification of the resulting precipitate and adding a dextran sulfate in an amount effective to potentiate the plasminogen activator.

6. A pharmaceutical composition according to claim 5 in which the salt used for precipitation in stages (c), (d) and (e) is crystalline ammonium sulphate.

7. A pharmaceutical composition according to claim 6 in which the ammonium sulphate is used in stage (c) at a concentration of between about 200 and about 300 g/l and in stages (d) and (e) at a concentration of between about 60 and about 80 g/l.

8. A pharmaceutical composition according to claim 5 in which the stage of purification is carried out by precipitation of the activator at a pH of between about 6.3 and about 6.5 and by affinity chromatography of the precipitate obtained after it has been taken up in solution.

9. A pharmaceutical composition according to claim 5 in which the plasminogen activator and the dextran sulphate are prepared in the form of a complex by addition of the dextron sulphate to the activator in solution at a pH close to neutrality and the complex is then precipitated by acidification of the solution to a pH of about 6.

10. A pharmaceutical composition according to claim 5 in which the dextran sulphate has a molecular weight of between about 3000 and about 1500 and contains between about 10 and about 20% of sulphur.

11. A pharmaceutical composition according to claim 5 in which the dextran sulphate is used in an amount of between about 10 and about 30% by weight of the activator determined as protein.

* * * * *